United States Patent
Coruzzi et al.

(10) Patent No.: US 11,414,715 B2
(45) Date of Patent: Aug. 16, 2022

(54) NUTRIENT SENSING IN CROP PRODUCTION

(71) Applicant: New York University, New York, NY (US)

(72) Inventors: Gloria M. Coruzzi, New York, NY (US); Joseph Swift, Jersey City, NJ (US)

(73) Assignee: New York University, New York, NY (US)

( * ) Notice: Subject to any disclaimer, the term of this patent is extended or adjusted under 35 U.S.C. 154(b) by 85 days.

(21) Appl. No.: 16/204,558

(22) Filed: Nov. 29, 2018

(65) Prior Publication Data

US 2019/0161812 A1 May 30, 2019

Related U.S. Application Data

(60) Provisional application No. 62/592,185, filed on Nov. 29, 2017.

(51) Int. Cl.
*C12Q 1/6895* (2018.01)
*C12N 15/82* (2006.01)
*A01H 1/04* (2006.01)
*C07K 14/415* (2006.01)

(52) U.S. Cl.
CPC .............. *C12Q 1/6895* (2013.01); *A01H 1/04* (2013.01); *C07K 14/415* (2013.01); *C12N 15/8261* (2013.01); *C12Q 2600/13* (2013.01); *C12Q 2600/158* (2013.01)

(58) Field of Classification Search
None
See application file for complete search history.

(56) References Cited

U.S. PATENT DOCUMENTS

2001/0053519 A1 * 12/2001 Fodor .................. B82Y 30/00
536/24.1

OTHER PUBLICATIONS

Li et al. Metabolic and transcriptomic signatures of rice floral organs reveal sugar starvation as a factor in reproductive failure under heat and drought stress.Plant, Cell and Environment (2015) 38, 2171-2192. (Year: 2015).*
The information of microarray GPL18620. NCBI GEO platform GPL18620, Affymetrix Rice Genome Array (custom CDF; RAGP7) (Public on May 31, 2015) [Retrieved on Aug. 7, 2020]. Retrieved from the internet: <https://www.ncbi.nlm.nih.gov/geo/query/acc.cgi?acc=GPL18620>. (Year: 2015).*
NCBI GEO platform GPL18620, Affymetrix Rice Genome Array Full Table View (Public on May 31, 2015) [Retrieved on Aug. 7, 2020]. Retrieved from the internet: <https://www.ncbi.nlm.nih.gov/geo/query/acc.cgi?view=data&acc=GPL18620&id=3445&db=GeoDb_blob111>. (Year: 2015).*
Li et al. Plant, Cell and Environment; 2015; 38: 2171-2192. (Year: 2015).*
Chen et al. BMC Research Notes; 2014, 7; 15: p. 1-9. (Year: 2014).*

* cited by examiner

*Primary Examiner* — Dave T Nguyen
*Assistant Examiner* — Wahwah T Johnson
(74) *Attorney, Agent, or Firm* — Hodgson Russ LLP

(57) ABSTRACT

Provided are methods and mRNA expression chips for identifying genes that are defined by certain nitrogen and water content relationships in soil. The genes can be up or down regulated under low nitrogen or arid conditions to increase the yield or biomass of crops.

3 Claims, 17 Drawing Sheets
(9 of 17 Drawing Sheet(s) Filed in Color)

| Cultivar | Subgroup |
|---|---|
| Haginomae Mochi | Japonica |
| Nipponbare | Japonica |
| PR106 | Indica |
| BG90-2 | Indica |
| Tainung 67 | Japonica |
| Beonjo | Japonica |
| IR20 | Indica |
| IR83388-B-B-108-3 | Indica |
| IR83383-B-B-129-4 | Indica |
| Palawan | Indica |
| BG34-8 | Indica |
| PSBRC 82 | Indica |
| IR74371-54-1-1 | Indica-Japonica |
| IR87707-445-B-B-B | Indica |
| Yabani Montakhab | Japonica |
| BG380-2 | Indica |
| IR64 | Indica |
| IR74371-70-1-1 | Indica-Japonica |
| IR83380-B-B-124-1 | Indica |

Figure 7

| Gene | Model Fit | Biomass Association | Yield Association |
|---|---|---|---|
| LOC_Os01g03030 | N/W | Down regulated | Down regulated |
| LOC_Os01g06310 | N/W | Down regulated | Down regulated |
| LOC_Os01g12840 | N/W | Up regulated | Up regulated |
| LOC_Os01g27150 | N/W | Up regulated | Up regulated |
| LOC_Os01g36950 | N/W | Down regulated | Down regulated |
| LOC_Os01g47760 | N/W | Down regulated | Down regulated |
| LOC_Os01g61010 | N/W | Up regulated | Up regulated |
| LOC_Os01g61080 | N/W | Up regulated | Up regulated |
| LOC_Os01g62870 | N/W | Up regulated | Up regulated |
| LOC_Os01g70170 | N/W | Down regulated | Down regulated |
| LOC_Os02g13190 | N/W | Up regulated | Up regulated |
| LOC_Os02g15800 | N/W | Down regulated | Down regulated |
| LOC_Os02g39884 | N/W | Down regulated | Down regulated |
| LOC_Os03g02450 | N/W | Down regulated | Down regulated |
| LOC_Os03g16920 | N/W | Down regulated | Down regulated |
| LOC_Os03g24220 | N/W | Up regulated | Up regulated |
| LOC_Os03g44620 | N/W | Up regulated | Up regulated |
| LOC_Os03g47930 | N/W | Up regulated | Up regulated |
| LOC_Os03g55320 | N/W | Down regulated | Down regulated |
| LOC_Os03g60560 | N/W | Down regulated | Down regulated |
| LOC_Os03g63310 | N/W | Down regulated | Down regulated |
| LOC_Os04g10690 | N/W | Down regulated | Down regulated |
| LOC_Os04g32740 | N/W | Down regulated | Down regulated |
| LOC_Os04g35540 | N/W | Up regulated | Up regulated |
| LOC_Os04g44610 | N/W | Up regulated | Down regulated |
| LOC_Os04g46180 | N/W | Down regulated | Up regulated |
| LOC_Os04g55720 | N/W | Down regulated | Down regulated |
| LOC_Os05g25850 | N/W | Down regulated | Down regulated |
| LOC_Os05g31020 | N/W | Down regulated | Down regulated |
| LOC_Os05g41480 | N/W | Down regulated | Down regulated |
| LOC_Os05g50090 | N/W | Up regulated | Up regulated |
| LOC_Os05g50570 | N/W | Up regulated | Down regulated |
| LOC_Os06g01440 | N/W | Up regulated | Up regulated |
| LOC_Os06g03540 | N/W | Up regulated | Up regulated |
| LOC_Os06g08110 | N/W | Down regulated | Down regulated |
| LOC_Os06g11450 | N/W | Down regulated | Down regulated |
| LOC_Os06g13030 | N/W | Up regulated | Up regulated |

Figure 8 (cont.)

| Gene | Model Fit | Biomass Association | Yield Association |
|---|---|---|---|
| LOC_Os07g18874 | N/W | Down regulated | Up regulated |
| LOC_Os07g38270 | N/W | Down regulated | Down regulated |
| LOC_Os07g44910 | N/W | Down regulated | Down regulated |
| LOC_Os07g47140 | N/W | Down regulated | Up regulated |
| LOC_Os08g08820 | N/W | Up regulated | Up regulated |
| LOC_Os09g31400 | N/W | Up regulated | Up regulated |
| LOC_Os09g39940 | N/W | Down regulated | Down regulated |
| LOC_Os10g09240 | N/W | Down regulated | Down regulated |
| LOC_Os10g12130 | N/W | Down regulated | Up regulated |
| LOC_Os11g05780 | N/W | Up regulated | Up regulated |
| LOC_Os11g08210 | N/W | Down regulated | Down regulated |
| LOC_Os11g32480 | N/W | Down regulated | Up regulated |
| LOC_Os11g37520 | N/W | Down regulated | Down regulated |
| LOC_Os11g40570 | N/W | Down regulated | Up regulated |
| LOC_Os12g03370 | N/W | Down regulated | Up regulated |
| LOC_Os12g29400 | N/W | Down regulated | Down regulated |
| LOC_Os12g43640 | N/W | Down regulated | Down regulated |
| LOC_Os01g04900 | NxW | Down regulated | Down regulated |
| LOC_Os01g07310 | NxW | Up regulated | Up regulated |
| LOC_Os01g13100 | NxW | Up regulated | Up regulated |
| LOC_Os01g31690 | NxW | Up regulated | Up regulated |
| LOC_Os01g39960 | NxW | Up regulated | Up regulated |
| LOC_Os01g41710 | NxW | Up regulated | Up regulated |
| LOC_Os01g47270 | NxW | Up regulated | Up regulated |
| LOC_Os01g50860 | NxW | Down regulated | Down regulated |
| LOC_Os01g51360 | NxW | Up regulated | Up regulated |
| LOC_Os01g54390 | NxW | Up regulated | Up regulated |
| LOC_Os01g54560 | NxW | Up regulated | Up regulated |
| LOC_Os01g59080 | NxW | Up regulated | Up regulated |
| LOC_Os01g67000 | NxW | Up regulated | Down regulated |
| LOC_Os01g68330 | NxW | Up regulated | Up regulated |
| LOC_Os01g69950 | NxW | Down regulated | Up regulated |
| LOC_Os01g69980 | NxW | Up regulated | Up regulated |
| LOC_Os01g72980 | NxW | Up regulated | Down regulated |
| LOC_Os01g73580 | NxW | Up regulated | Up regulated |
| LOC_Os01g74280 | NxW | Up regulated | Up regulated |
| LOC_Os02g02870 | NxW | Up regulated | Up regulated |

Figure 8 (cont.)

| Gene | Model Fit | Biomass Association | Yield Association |
|---|---|---|---|
| LOC_Os02g03250 | NxW | Up regulated | Up regulated |
| LOC_Os02g03740 | NxW | Up regulated | Up regulated |
| LOC_Os02g03850 | NxW | Down regulated | Up regulated |
| LOC_Os02g09150 | NxW | Up regulated | Up regulated |
| LOC_Os02g10450 | NxW | Down regulated | Up regulated |
| LOC_Os02g15870 | NxW | Up regulated | Down regulated |
| LOC_Os02g15950 | NxW | Down regulated | Down regulated |
| LOC_Os02g22100 | NxW | Up regulated | Up regulated |
| LOC_Os02g22820 | NxW | Up regulated | Up regulated |
| LOC_Os02g38240 | NxW | Up regulated | Up regulated |
| LOC_Os02g39710 | NxW | Up regulated | Up regulated |
| LOC_Os02g42570 | NxW | Up regulated | Up regulated |
| LOC_Os02g44920 | NxW | Up regulated | Up regulated |
| LOC_Os02g45070 | NxW | Up regulated | Up regulated |
| LOC_Os02g50620 | NxW | Up regulated | Up regulated |
| LOC_Os02g51080 | NxW | Up regulated | Up regulated |
| LOC_Os02g55610 | NxW | Up regulated | Up regulated |
| LOC_Os02g56040 | NxW | Up regulated | Down regulated |
| LOC_Os02g56580 | NxW | Up regulated | Up regulated |
| LOC_Os02g57030 | NxW | Up regulated | Up regulated |
| LOC_Os02g57790 | NxW | Up regulated | Up regulated |
| LOC_Os02g58070 | NxW | Up regulated | Up regulated |
| LOC_Os02g58180 | NxW | Up regulated | Up regulated |
| LOC_Os02g58250 | NxW | Up regulated | Up regulated |
| LOC_Os03g01920 | NxW | Up regulated | Up regulated |
| LOC_Os03g02600 | NxW | Up regulated | Up regulated |
| LOC_Os03g03720 | NxW | Up regulated | Down regulated |
| LOC_Os03g07370 | NxW | Up regulated | Up regulated |
| LOC_Os03g08070 | NxW | Up regulated | Up regulated |
| LOC_Os03g10850 | NxW | Down regulated | Up regulated |
| LOC_Os03g10880 | NxW | Up regulated | Up regulated |
| LOC_Os03g13010 | NxW | Up regulated | Up regulated |
| LOC_Os03g14669 | NxW | Up regulated | Up regulated |
| LOC_Os03g15460 | NxW | Down regulated | Up regulated |
| LOC_Os03g15690 | NxW | Up regulated | Up regulated |
| LOC_Os03g18160 | NxW | Up regulated | Up regulated |
| LOC_Os03g18710 | NxW | Up regulated | Up regulated |

Figure 8 (cont.)

| Gene | Model Fit | Biomass Association | Yield Association |
|---|---|---|---|
| LOC_Os03g22330 | NxW | Up regulated | Up regulated |
| LOC_Os03g22370 | NxW | Up regulated | Up regulated |
| LOC_Os03g24950 | NxW | Up regulated | Up regulated |
| LOC_Os03g25940 | NxW | Up regulated | Up regulated |
| LOC_Os03g28420 | NxW | Up regulated | Up regulated |
| LOC_Os03g29680 | NxW | Up regulated | Up regulated |
| LOC_Os03g36540 | NxW | Up regulated | Up regulated |
| LOC_Os03g36750 | NxW | Up regulated | Up regulated |
| LOC_Os03g39610 | NxW | Up regulated | Up regulated |
| LOC_Os03g41120 | NxW | Up regulated | Up regulated |
| LOC_Os03g48170 | NxW | Down regulated | Up regulated |
| LOC_Os03g52010 | NxW | Up regulated | Up regulated |
| LOC_Os03g52660 | NxW | Up regulated | Up regulated |
| LOC_Os03g56420 | NxW | Up regulated | Up regulated |
| LOC_Os03g56950 | NxW | Up regulated | Up regulated |
| LOC_Os03g57240 | NxW | Up regulated | Up regulated |
| LOC_Os03g60500 | NxW | Down regulated | Up regulated |
| LOC_Os03g62370 | NxW | Down regulated | Down regulated |
| LOC_Os03g62780 | NxW | Up regulated | Up regulated |
| LOC_Os03g63360 | NxW | Down regulated | Up regulated |
| LOC_Os03g63480 | NxW | Up regulated | Up regulated |
| LOC_Os04g21350 | NxW | Up regulated | Up regulated |
| LOC_Os04g33080 | NxW | Up regulated | Up regulated |
| LOC_Os04g38410 | NxW | Up regulated | Up regulated |
| LOC_Os04g38870 | NxW | Up regulated | Up regulated |
| LOC_Os04g38960 | NxW | Up regulated | Up regulated |
| LOC_Os04g42020 | NxW | Up regulated | Up regulated |
| LOC_Os04g57330 | NxW | Up regulated | Up regulated |
| LOC_Os05g01090 | NxW | Up regulated | Up regulated |
| LOC_Os05g02500 | NxW | Up regulated | Up regulated |
| LOC_Os05g07130 | NxW | Up regulated | Up regulated |
| LOC_Os05g07870 | NxW | Up regulated | Up regulated |
| LOC_Os05g08930 | NxW | Down regulated | Up regulated |
| LOC_Os05g14270 | NxW | Up regulated | Up regulated |
| LOC_Os05g23420 | NxW | Up regulated | Up regulated |
| LOC_Os05g28730 | NxW | Up regulated | Down regulated |
| LOC_Os05g33840 | NxW | Up regulated | Up regulated |

Figure 8 (cont.)

| Gene | Model Fit | Biomass Association | Yield Association |
|---|---|---|---|
| LOC_Os05g34650 | NxW | Up regulated | Up regulated |
| LOC_Os05g36270 | NxW | Up regulated | Up regulated |
| LOC_Os05g41190 | NxW | Up regulated | Up regulated |
| LOC_Os05g43310 | NxW | Up regulated | Up regulated |
| LOC_Os05g47560 | NxW | Up regulated | Up regulated |
| LOC_Os05g48630 | NxW | Up regulated | Up regulated |
| LOC_Os05g49880 | NxW | Down regulated | Up regulated |
| LOC_Os06g05380 | NxW | Up regulated | Up regulated |
| LOC_Os06g08090 | NxW | Up regulated | Up regulated |
| LOC_Os06g10650 | NxW | Up regulated | Up regulated |
| LOC_Os06g11040 | NxW | Up regulated | Up regulated |
| LOC_Os06g21590 | NxW | Up regulated | Up regulated |
| LOC_Os06g24070 | NxW | Up regulated | Up regulated |
| LOC_Os06g34100 | NxW | Up regulated | Up regulated |
| LOC_Os06g39140 | NxW | Up regulated | Up regulated |
| LOC_Os06g39344 | NxW | Up regulated | Down regulated |
| LOC_Os06g39370 | NxW | Down regulated | Up regulated |
| LOC_Os06g43130 | NxW | Up regulated | Up regulated |
| LOC_Os06g43430 | NxW | Up regulated | Up regulated |
| LOC_Os06g47310 | NxW | Up regulated | Up regulated |
| LOC_Os06g47930 | NxW | Up regulated | Up regulated |
| LOC_Os06g47940 | NxW | Up regulated | Up regulated |
| LOC_Os06g48500 | NxW | Up regulated | Up regulated |
| LOC_Os07g04840 | NxW | Up regulated | Up regulated |
| LOC_Os07g07900 | NxW | Up regulated | Up regulated |
| LOC_Os07g08770 | NxW | Down regulated | Up regulated |
| LOC_Os07g15670 | NxW | Down regulated | Up regulated |
| LOC_Os07g18720 | NxW | Up regulated | Up regulated |
| LOC_Os07g25430 | NxW | Up regulated | Up regulated |
| LOC_Os07g27490 | NxW | Down regulated | Up regulated |
| LOC_Os07g33350 | NxW | Up regulated | Up regulated |
| LOC_Os07g36190 | NxW | Up regulated | Up regulated |
| LOC_Os07g37240 | NxW | Up regulated | Up regulated |
| LOC_Os07g37250 | NxW | Up regulated | Up regulated |
| LOC_Os07g43980 | NxW | Up regulated | Up regulated |
| LOC_Os07g48410 | NxW | Up regulated | Up regulated |
| LOC_Os08g03310 | NxW | Up regulated | Up regulated |

Figure 8 (cont.)

| Gene | Model Fit | Biomass Association | Yield Association |
|---|---|---|---|
| LOC_Os08g14450 | NxW | Up regulated | Down regulated |
| LOC_Os08g16830 | NxW | Up regulated | Up regulated |
| LOC_Os08g23780 | NxW | Up regulated | Down regulated |
| LOC_Os08g35160 | NxW | Up regulated | Up regulated |
| LOC_Os08g40160 | NxW | Up regulated | Up regulated |
| LOC_Os08g40500 | NxW | Up regulated | Up regulated |
| LOC_Os08g40510 | NxW | Up regulated | Up regulated |
| LOC_Os08g41830 | NxW | Up regulated | Up regulated |
| LOC_Os08g44050 | NxW | Up regulated | Up regulated |
| LOC_Os08g44680 | NxW | Up regulated | Up regulated |
| LOC_Os09g06740 | NxW | Down regulated | Up regulated |
| LOC_Os09g25580 | NxW | Down regulated | Down regulated |
| LOC_Os09g28390 | NxW | Down regulated | Up regulated |
| LOC_Os09g29130 | NxW | Up regulated | Up regulated |
| LOC_Os09g35880 | NxW | Up regulated | Up regulated |
| LOC_Os09g39180 | NxW | Up regulated | Up regulated |
| LOC_Os10g33840 | NxW | Up regulated | Down regulated |
| LOC_Os10g35010 | NxW | Down regulated | Up regulated |
| LOC_Os10g35110 | NxW | Up regulated | Up regulated |
| LOC_Os10g35150 | NxW | Up regulated | Up regulated |
| LOC_Os10g39440 | NxW | Up regulated | Up regulated |
| LOC_Os10g41780 | NxW | Up regulated | Up regulated |
| LOC_Os11g02610 | NxW | Up regulated | Up regulated |
| LOC_Os11g03390 | NxW | Up regulated | Up regulated |
| LOC_Os11g07030 | NxW | Up regulated | Up regulated |
| LOC_Os11g10990 | NxW | Up regulated | Up regulated |
| LOC_Os11g11050 | NxW | Up regulated | Up regulated |
| LOC_Os11g13890 | NxW | Up regulated | Up regulated |
| LOC_Os11g28270 | NxW | Up regulated | Up regulated |
| LOC_Os11g29900 | NxW | Up regulated | Up regulated |
| LOC_Os11g32160 | NxW | Down regulated | Up regulated |
| LOC_Os11g39640 | NxW | Up regulated | Up regulated |
| LOC_Os11g40070 | NxW | Up regulated | Down regulated |
| LOC_Os11g41890 | NxW | Down regulated | Down regulated |
| LOC_Os11g42350 | NxW | Down regulated | Up regulated |
| LOC_Os11g47920 | NxW | Up regulated | Up regulated |
| LOC_Os12g03070 | NxW | Up regulated | Up regulated |

Figure 8 (cont.)

| Gene | Model Fit | Biomass Association | Yield Association |
|---|---|---|---|
| LOC_Os12g04480 | NxW | Up regulated | Up regulated |
| LOC_Os12g05550 | NxW | Up regulated | Up regulated |
| LOC_Os12g06850 | NxW | Up regulated | Up regulated |
| LOC_Os12g07020 | NxW | Down regulated | Up regulated |
| LOC_Os12g08130 | NxW | Up regulated | Up regulated |
| LOC_Os12g08730 | NxW | Up regulated | Up regulated |
| LOC_Os12g08770 | NxW | Up regulated | Up regulated |
| LOC_Os12g09250 | NxW | Down regulated | Down regulated |
| LOC_Os12g13120 | NxW | Up regulated | Up regulated |
| LOC_Os12g18900 | NxW | Up regulated | Up regulated |
| LOC_Os12g23200 | NxW | Up regulated | Up regulated |
| LOC_Os12g33080 | NxW | Up regulated | Up regulated |
| LOC_Os12g34860 | NxW | Down regulated | Down regulated |
| LOC_Os12g38640 | NxW | Up regulated | Up regulated |
| LOC_Os12g40500 | NxW | Up regulated | Down regulated |
| LOC_Os12g44150 | NxW | Up regulated | Up regulated |

Figure 8 (cont.)

NUTRIENT SENSING IN CROP PRODUCTION

CROSS-REFERENCE TO RELATED APPLICATIONS

This application claims priority to U.S. Provisional Application No. 62/592,185, filed on Nov. 29, 2017, the disclosure of which is incorporated herein by reference.

FIELD OF THE DISCLOSURE

This disclosure generally relates to sensing of nitrogen and water for crop production, and more particularly defines relationships between nitrogen, water and crop production for altering yield and biomass.

BACKGROUND OF THE DISCLOSURE

Nitrogen (N) and Water (W) availability in marginal soils limits crop production world-wide. While N and W interact to regulate plant growth, little is known about the underlying sensing mechanisms. To feed a further 2 billion people by 2050, food production on marginal soils needs to rise dramatically (Godfray et al., Science, 2010, 327(5967):812-818. Across continents, marginal soils lack enough water (W) and nitrogen (N) to sustain high growth (Gibbs et al., Applied Geography, 2015, 57:12-21). Thus, breeding or engineering crops adapted to soils poor in both N and W is a pressing global need.

SUMMARY OF THE DISCLOSURE

The present disclosure identifies mechanisms underlying N and W sensing in crops. Using rice, a crop staple that feeds 3.5 billion people world-wide, as an example, this disclosure describes the relationships between N and W and plant biomass and yield, and based on these relationships, provides compositions, materials and methods directed to identifying and affecting the expression of genes that are defined by complex N and W interactions. Methods and compositions are also provided for improving crop production under inadequate N or W conditions.

In an aspect, this disclosure provides a method of optimizing or predicting plant biomass changes in soil, wherein the soil contains low levels of nitrogen and/or wherein the soil is arid, comprising determining expression of one or more genes listed in FIG. 8 and comparing the expression level in a plant with desired biomass (such as a control), and further optionally inducing or repressing expression of one or more specific genes to achieve the desired biomass.

In an aspect, this disclosure provides a method of identifying gene biomarkers that can increase plant biomass in a soil that contains low levels of nitrogen and/or arid soil comprising determining gene expression that is exclusively defined by a relationships of N and W, such as N/W or N×W.

In as aspect, this disclosure provides an mRNA expression chip containing one or more polynucleotides that are useful for affecting plant biomass and whose expression is defined by N/W or N×W models.

In an embodiment, this disclosure provides a method of predicting plant biomass comprising determining the expression of genes in the field or in the lab, wherein the genes are one or more of LOC_Os10g09240, LOC_Os12g29400 (ABA-response protein), LOC_Os05g31020 (eRF peptide change release factor), LOC_Os03g57240 (C2H2 Transcription factor), LOC_Os01g51360 (Lipase).

In an embodiment, this disclosure provides a method of increasing biomass or yield by altering (increasing or decreasing) the expression of one or more of LOC_Os10g09240, LOC_Os12g29400 (ABA-response protein), LOC_Os05g31020 (eRF peptide change release factor), LOC_Os03g57240 (C2H2 Transcription factor), LOC_Os01g51360 (Lipase).

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 7. List of 19 rice cultivars grown in the field. Cultivars were chosen based on reports of being N-use efficient or W-use efficient either in literature or from prior field observations.

FIG. 8. Table showing N×W and N/W rice gene biomarkers.

DESCRIPTION OF THE DISCLOSURE

Figure 1:
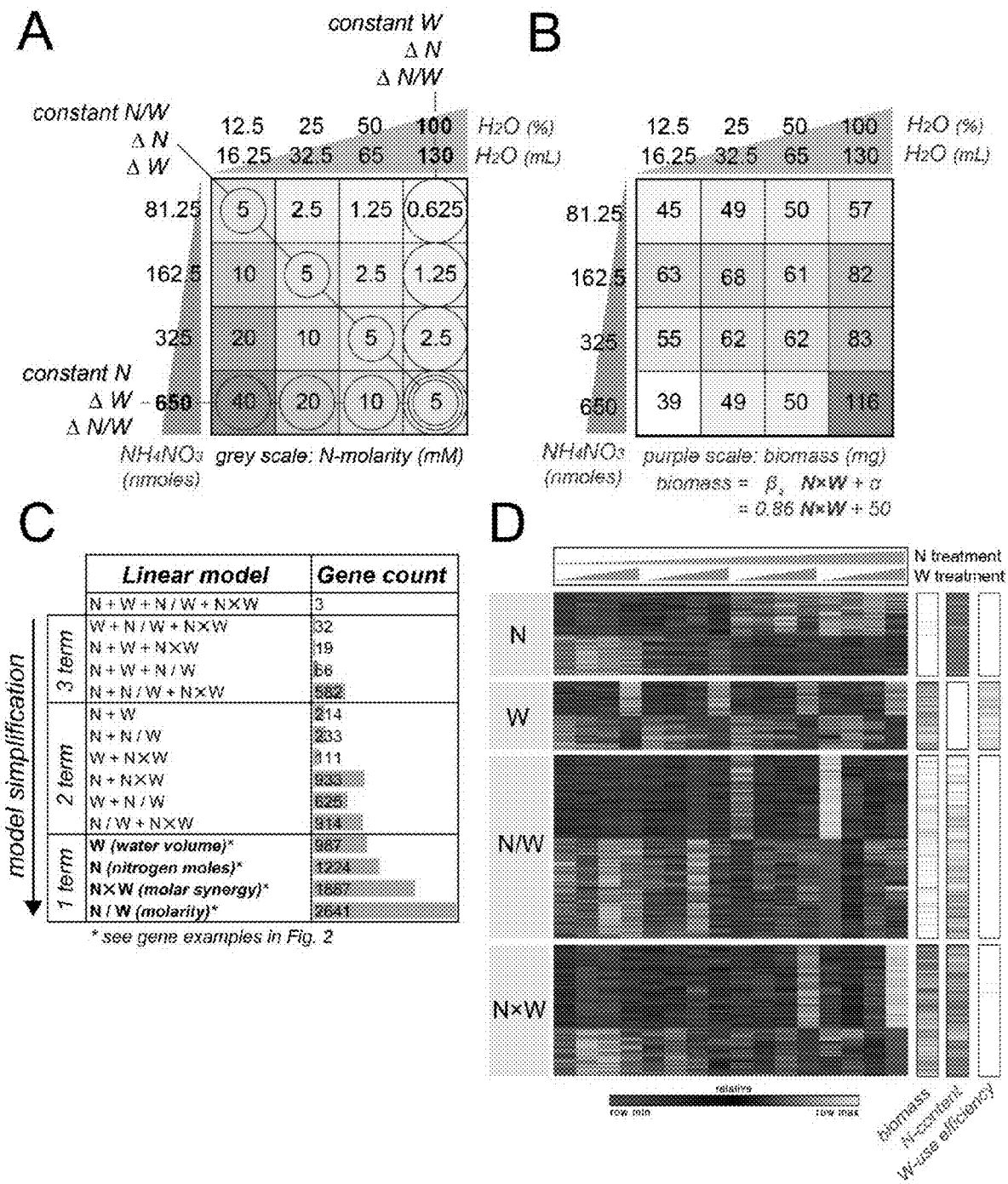
FIG. 1. A factorial design varying Nitrogen (N) and Water (W) amounts uncovers rice responses to N-moles, W-volume, N-molarity (N/W) and the synergistic interaction 'N×W'. A: A 4-by-4 factorial matrix that varies both N-moles and W-volume can distinguish plant responses to N-moles, W-volume and N-molarity. B: A synergistic effect between N-moles and W-volume, modeled by the N×W interaction term, best explains changes in shoot biomass (linear model p-value=$1.3\times10^{-5}$) C: Through model simplification, 14 linear models uncovered genome-wide responses to N-moles, W-volume, N/W (molarity), N×W, and their combinations (adjusted p-value <0.005). D: Expression heatmap of genes fitted by a single model term, and the proportion of genes within each class that significantly correlated with biomass, leaf N-content and leaf W-use efficiency (adjusted p-value <0.05).

Except defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

This disclosure includes all nucleotide sequences referenced herein, all proteins encoded by those sequences, all homologs of the proteins and all sequences encoding the homologous proteins, and all sequences that are from 50%-99% identical to the sequences described or referenced herein. For example, this disclosure includes all nucleotide sequences and all proteins encoded by those sequences, all homologs of the proteins and all sequences encoding the homologous proteins, and all sequences that are 60, 70, 80, 90, 95, 96, 97, 98 or 99% identical to the sequences described or referenced herein. The identity may be determined across the entire sequence, or a segment thereof that retains its intended function. The disclosure includes all complementary nucleotide sequences, and all cDNA sequences of mRNA sequences.

In certain embodiments, the disclosure provides genetic loci. The sequences of the loci, and RNA sequences encoded by such sequences, and the proteins encoded by such sequences, are known in the art and can be accessed using publically available resources. As an example, the sequence of any genetic loci described herein can be accessed using a database accessible at rice.plantbiology.msu.edu/analyses search locus.shtml. The sequences of the loci described in the specification, figures and tables of this disclosure and that are accessible in this database are incorporated herein by reference as they exist in the database on the priority date of this application or patent, including but not limited to the sequences of genes that are present in the loci.

This disclosure is based on our findings of combinatorial sensing of N and W in plants, using multivariate linear models to model global gene expression patterns in rice seedlings exposed to a complete matrix of N and W doses. This genome-wide read-out supports three modalities of N and W sensing: Moles (N or W), Molarity (N/W), and Molar Synergy (N×W).

Surprisingly, little is known about how N and W nutrient signals interact to regulate plant growth. Studying this interaction is not trivial; since W acts as a solvent for N uptake, N and W cannot be assumed to act as independent signals. The present disclosure provides methods for identifying chemical relationships between nitrogen (N) and water (W) to predict biomass, and yield. Based on the relationships identified herein, predictions of biomass and yield can be made for different soil and environmental conditions where N and W availability may vary. This information may be helpful in identifying suitable varieties of a crop under given conditions or identifying suitable soil conditions for a given crop variety. The disclosure also provides a set of genes that have been identified as relevant for predicting biomass and yield. Determination of expression of one or more of these genes can be carried out to make predictions relating to biomass.

We observed that gene responses to N×W or N/W detected in lab-grown rice, could accurately predict rice biomass in field tests of a variety of rice varieties. In an aspect, this disclosure provides a method for predicting biomass for crop production by identifying genes whose expression is defined by the relationship N/W or N×W. In an embodiment, the genes are ones whose expression is defined by the relationship [W+(N×W)]. Identification of a gene that follows this relationship can be carried out by identifying a gene that responds to both N and W status, where linear additions of N and W result in non-linear behavior of gene responses. The expression of the genes whose expression is defined by this relationship may be altered to improve growth and yield outcomes. Thus, this combinatorial basis of nutrient sensing, and the genes defined by the relationship N×W and N/W have agronomic implications for developing crops with improved growth and yield outcomes on marginal low N, arid soils. In an embodiment, the genes defined by the relationship N×W and N/W are LOC_Os10g09240, LOC_Os12g29400 (ABA-response protein), LOC_Os05g31020 (eRF peptide change release factor), LOC_Os03g57240 (C2H2 Transcription factor), LOC_Os01g51360 (Lipase). Determining expression of the genes can be performed using standard techniques, such as PCR, QPCR, or RT-PCR assays for which general protocols are known in the art. Any sequence described herein, including DNA and cDNA sequences and RNA sequences, may be modified, such as by being attached to a substrate. Determining the expression of the genes can be performed using any of a variety of polynucleotide arrays. For example, arrays comprising reagents for detecting any, all, or any combinations of the genes disclosed herein can be used. Chips suitable for use in the present invention can be designed and made using known techniques and/or obtained from a variety of commercial chip vendors, such as Affymetrix, Illumina or Nanostring, given the benefit of the present disclosure. In one embodiment, a chip design will provide for measuring expression of at least one or two or more genes described herein. In embodiments, the chip is an mRNA expression chip. For example, a suitable chip can be designed for measuring the expression of one or more of the genes listed in FIG. 8. This is a list of 238 genes that are defined by the relationship N×W or N/W. In one embodiment, the chip design will provide for assaying one or more, or any combination or sub-combinations, of the 238 genes listed in FIG. 8. In one embodiment, the genes are one or more of LOC_Os10g09240, LOC_Os12g29400 (ABA-response protein), LOC_Os05g31020 (eRF peptide change release factor), LOC_Os03g57240 (C2H2 Transcription factor), LOC_Os01g51360 (Lipase). Thus, in one embodiment, a gene chip can be designed that will provide for assaying one or more of LOC_Os10g09240, LOC_Os12g29400 (ABA-response protein), LOC_Os05g31020 (eRF peptide change release factor), LOC_Os03g57240 (C2H2 Transcription factor), LOC_Os01g51360 (Lipase).

In one aspect, the disclosure includes a plurality of isolated and/or synthetic probes which are complementary to, and thus can hybridize to, a combination of gene markers described herein, such as in FIG. 8. In an embodiment, the genes are LOC_Os10g09240, LOC_Os12g29400 (ABA-response protein), LOC_Os05g31020 (eRF peptide change release factor), LOC_Os03g57240 (C2H2 Transcription factor), LOC_Os01g51360 (Lipase). By using a plurality of probes, a plurality of the gene markers can be measured in a single assay. The plurality of probes can be reversibly or irreversibly attached to a substrate to facilitate performance of any suitable marker expression assay. In various embodiments, the disclosure includes a plurality of isolated and/or synthetic probes which can be used as PCR-based primers for amplification of the markers, or for amplification of any detectable segment of them. In various embodiments, the PCR primers can be such that any one, or any combination, or all of the markers can be detected in, for instance, a single or multiplex PCR multiplex assays. Primers can be designed using well known criteria, such as the length, GC content, melting temperature, etc.

In an embodiment, the disclosure provides an mRNA expression chip comprising probes that can detect the expression level of one or more of the 238 genes listed in the table in FIG. 8. This table also indicates if the expression of a gene is upregulated or down regulated with N and W conditions, and the N, W relationship that describes the gene expression. From this table, genes whose expression needs to be increased or decreased to increase biomass or yield can be identified. These genes were identified by the N×W and N/W models. In one embodiment, the mRNA expression chip contains probes that can detect the expression level of one or more of LOC_Os10g09240, LOC_Os12g29400 (ABA-response protein), LOC_Os05g31020 (eRF peptide change release factor), LOC_Os03g57240 (C2H2 Transcription factor), LOC_Os01g51360 (Lipase)

As used herein "low N" signifies that there is not enough N for crops to meet yield potential (maximum yield) and "arid" signifies that there is not enough water for crops to meet yield potential. In an embodiment, "arid" conditions define soils with a water potential less than field capacity. In an example, the water potential can be less than −3000 kPa. For example, arid condition can indicate water potential of −0.01 kPa to −3000 kPa. In an example, the water potential can be from −0.01 kPa to −2, −5, −10, −15, −50, −100, −500, −1000, −1500, −2000, −2500 or −3000 kPa. In an embodiment, "low N" conditions define soil N values (measured at depths 0-100 cm) that are between 0 and 0.1%, or nitrate levels between 0 and 20 ppm. In an embodiment, the N levels (measured at depths from 0 to 100 cm) are from 0.001 to 0.1% and/or nitrate levels are from 0.01 to 20 ppm. The disclosure also provides a method of identifying plants with an expression profile of under, over or normal expressed genes identified by the N/W and/or N×W models, or genes identified by the W+(N×W) model, wherein the genes are one or more of the genes listed in FIG. 8.

The disclosure provides a method for optimizing and/or predicting plant biomass and yield in soil, wherein the soil contains abnormal levels of nitrogen and/or abnormal levels of water. Abnormal levels can be higher or lower than normal for a given set of environment, such as a geographic location. The method comprises determining expression of one or more of the 238 genes found here to be relevant to the N×W and N/W models, or genes relevant to W+(N×W) model, and comparing the expression levels to normal or known biomass growth conditions.

In an embodiment, this disclosure provides a method of predicting plant biomass or yield in soil that contains low levels of nitrogen and/or is arid, comprising determining expression in the plant of one or more genes listed in FIG. 8 and comparing the expression level to a control, wherein up or down regulated expression of the gene compared to control, when referenced to FIG. 8 is indicative of whether the yield or biomass will be higher than normal. As an example, FIG. 8 table (and FIG. 4) indicate that when LOC_Os10g09240 is downregulated, biomass and yield are increased. As such a decrease in expression of LOC_Os10g09240 compared to control is predictive of an increase in biomass and yield. Similarly, FIG. 8 table indicates that when LOC_Os03g57240 is upregulated, biomass and yield are increased. As such, an increase in expression of LOC_Os03g57240 is predictive of an increase in biomass and yield. Similarly, referring to the table in FIG. 8, it can be determined if up or down regulation of a gene will be predictive of increased biomass or yield.

In an embodiment, this disclosure provides a method for increasing the yield and/or biomass of crops comprising increasing or decreasing the expression of one or more genes referring the correlation of the expression of the one or more genes with biomass or yield from FIG. 8. For example, the expression of genes that identified as being upregulated during increased yield or biomass can be induced, and/or the expression of genes that are indicated to be downregulated during increased biomass or yield in FIG. 8 can be reduced or eliminated to achieve a higher biomass or yield. As an example, FIG. 8 table indicates that when LOC_Os10g09240 is downregulated, biomass and yield are increased. As such the expression of LOC_Os10g09240 can be suppressed or eliminated to increase biomass and yield. Similarly, FIG. 8 table indicates that when LOC_Os03g57240 is upregulated, biomass and yield are increased. As such, the expression of LOC_Os03g57240 can be induced or over-expressed to increase in biomass and yield. Similarly, referring to the table in FIG. 8, it can be determined if up or down regulation of a gene will increase biomass or yield. Conversely, this information can also be used for decreasing the yield and/or biomass of crops comprising decreasing the expression of one or more genes from FIG. 8 that are identified as being upregulated during increased yield or biomass, or enhancing the expression of one or more genes from FIG. 8 that are downregulated during increased yield or biomass, or both.

Figure 4:
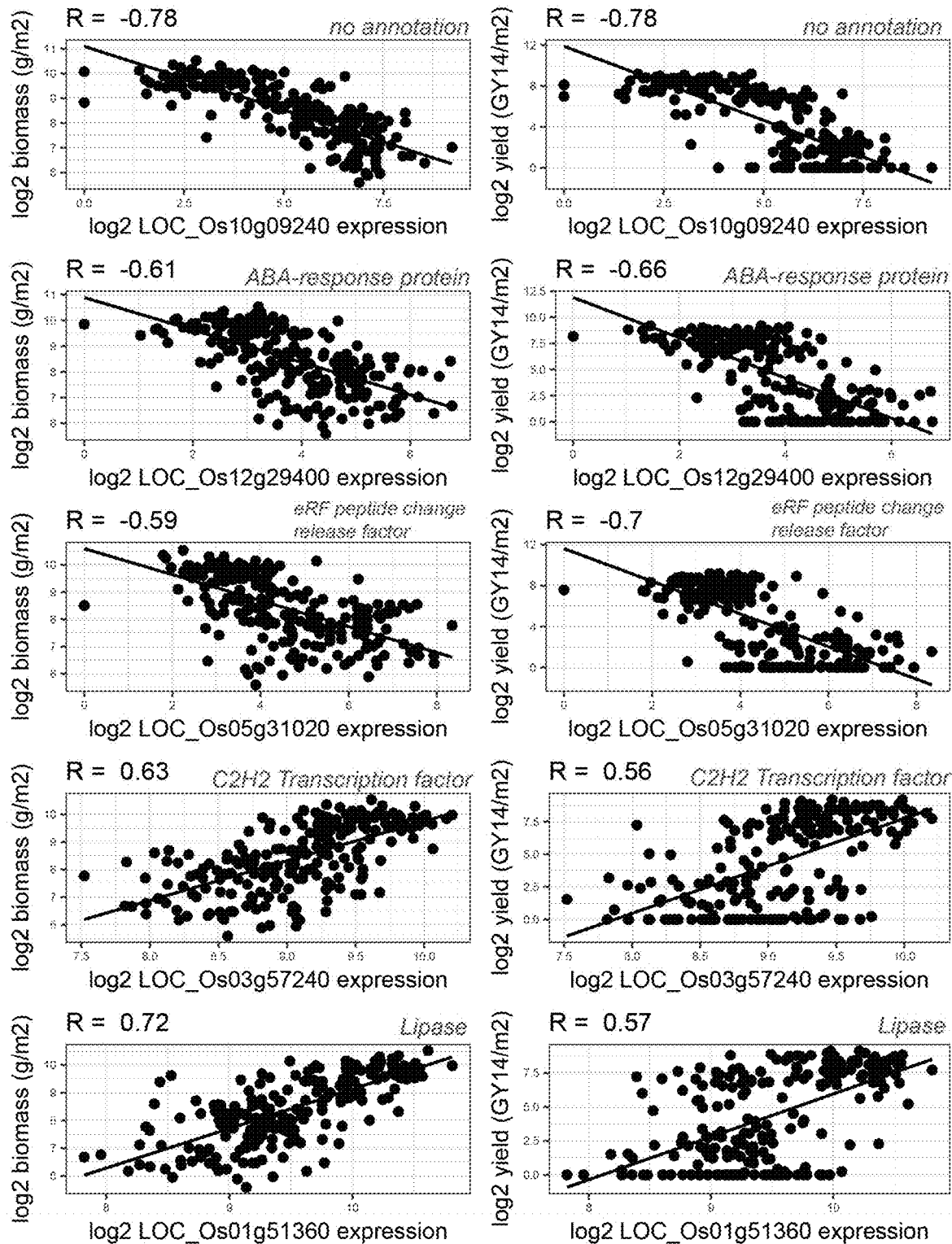
FIG. 4. Top 5 genes whose expression significantly predicts both biomass and yield outcomes.

In an embodiment, the disclosure provides a method for increasing the biomass or yield of a plant or crop comprising altering the expression of one or more of LOC_Os10g09240, LOC_Os12g29400 (ABA-response protein), LOC_Os05g31020 (eRF peptide change release factor), LOC_Os03g57240 (C2H2 Transcription factor), LOC_Os01g51360 (Lipase) wherein affecting the biomass can be increasing or decreasing and altering the expression can be over or under expression. The plant may be any plant. For example, in an embodiment, the plant may be a genus of *Arabidopsis*, *Oryza*, *Zea* or *Triticum*. As an example, down regulating or removing gene LOC_Os10g09240 would promote higher yield and biomass (FIG. 4 and FIG. 8 table). As another example, over expressing or up regulating gene LOC_Os03g57240 would promote higher yield and biomass (FIG. 4 and FIG. 8 table). The converse would be applicable for decreasing yield or biomass. Altering the expression of other genes to increase biomass or yield can similarly be made The disclosure provides a method of identifying gene biomarkers that are useful for maximizing plant biomass in soil, wherein the soil contains abnormal, such as lower than normal, levels of nitrogen and water. The gene markers may be identified by a N×W and N/W models, or any other relationship provided herein. Expression levels of these genes can be monitored to identify suitable crop varieties, or the expression of relevant genes may be induced by recombinant technologies.

While specific data and examples are provided herein with reference to rice, this disclosure is applicable to any plant and plant variety. Examples of plants include, but are not limited to plants from the genuses *Oryza*, *Zea* and *Triticum*. Other examples include plants from the genuses *Acorns*, *Aegilops*, *Allium*, *Amborella*, *Antirrhinum*, *Apium*, *Arabidopsis*, *Arachis*, *Beta*, *Betula*, *Brassica*, *Capsicum*, *Ceratopteris*, *Citrus*, *Cryptomeria*, *Cycas*, *Descurainia*, *Eschscholzia*, *Eucalyptus*, *Glycine*, *Gossypium*, *Hedyotis*, *Helianthus*, *Hordeum*, *Ipomoea*, *Lactuca*, *Linum*, *Liriodendron*, *Lotus*, *Lupinus*, *Lycopersicon*, *Medicago*, *Mesembryanthemum*, *Nicotiana*, *Nuphar*, *Pennisetum*, *Persea*, *Phaseolus*, *Physcomitrella*, *Picea*, *Pinus*, *Poncirus*, *Populus*, *Prunus*, *Robinia*, *Rosa*, *Saccharum*, *Schedonorus*, *Secale*, *Sesamum*, *Solanum*, *Sorghum*, *Stevia*, *Thellungiella*, *Theobroma*, *Triphysaria*, *Vitis*, or *Zinnia*.

The teachings of the present disclosure, including the genes identified can be used in over- or under expression in transgenic plants, and/or molecular breeding experiments to enhance biomass/yield in specific water and nitrogen conditions, such as, arid, low-N soils. Thus, in embodiments, the disclosure includes transgenic plants, and methods of making the transgenic plants, by introducing any nucleotide sequence described herein into a chromosome of a plant that is distinct from the plant that is the source of the nucleotide sequence.

In an aspect, this disclosure provides an mRNA expression chip containing one or more of the genes or segments thereof that are relevant for affecting plant biomass and whose expression is defined by the [W+(N×W)], N×W or N/W models. The mRNA expression chip, may comprise or consist of one or more of the genes listed in FIG. 8. In embodiments, an mRNA expression chip comprises a DNA microarray, the DNA in the microarray comprising all or segments of genes described herein, which can be bound with specificity by, for example, mRNA described herein, and/or cDNA produced from the mRNA. In embodiments, the DNA microarray is a cDNA array. In embodiments, the DNA segment of a gene is of adequate length to permit specific hybridization to a polynucleotide (an mRNA or a cDNA) that is to be analyzed. In embodiments, the DNA segment of a gene described herein that is present on the microarray comprises at least one exon. In embodiments, the segment of the gene is from 10-5,000 nucleotides, inclusive and including all integers and ranges of integers there between.

In embodiments, the disclosure includes contacting mRNA and/or cDNA produced from mRNA described herein with a DNA microarray to qualitatively or quantitatively determine expression of one or more of the mRNAs described herein. In embodiments, detectably labeled cDNA produced from mRNA described herein is used with an mRNA expression chip to determine whether or not any one or combination of genes described herein is expressed, and/or to determine whether or not expression of any gene(s) described herein changes in response to water, nitrogen, and/or water and nitrogen, and/or different proportions or ratios of water and nitrogen. In embodiments, the disclosure includes a DNA microarray with any one or combination of cDNAs described herein bound to DNA that is attached to the microarray. In embodiments, the disclosure comprises detecting a signal from a cDNA bound to DNA microarray, and may further comprise detecting signals based on the amount of distinct, labeled cDNAs, which may be labeled with different detectable labels. In embodiments, the detectably labeled cDNAs comprise fluorescent probes. In embodiments, separate fluorescent probes with distinct detectable labels are used. In embodiments, a reference probe can be used to determine the presence, absence or amount of expression of any gene described herein.

In an aspect, this disclosure provides a method of identifying plants with an expression profile of one or more of 238 genes, wherein the genes affect biomass defined by the relationship N×W or N/W such as listed in FIG. 8.

In an embodiment, this disclosure provides an mRNA expression chip containing one or more polynucleotides that are relevant for affecting plant biomass and whose expression is defined by N/W or N×W models. For example, the chip may contain a polynucleotide for detecting the expression of one or more genes listed in Table 8. In an example, the plant whose genes are detected may be a genus of *Arabidopsis*, *Oryza*, *Zea* or *Triticum*.

In an embodiment, this disclosure provides a method of identifying plants with a desired expression profile comprising identifying expression of one or more genes that affect biomass under the N/W or N×W models and are listed in FIG. 8, and selecting the plants that exhibit upregulated genes that are the same as those shown upregulated in FIG. 8, and/or that exhibit downregulated genes that are the same as those shown downregulated in FIG. 8.

In an embodiment, this disclosure provides a method of predicting plant biomass or yield in soil that contains low levels of nitrogen and/or wherein the soil is arid, comprising determining expression of one or more genes listed in FIG. 8 and comparing the expression level in a plant with a control. The control could be internal (such as another gene that is not responsive to N and W), or could be external, such as comparing it to another plant that is not grown with N and W stress, or some other control. If one or more genes defined by the N and W relationships as described herein, such as those in FIG. 8, are up or down regulated compared to control, then reference to FIG. 8 will indicate if the up or downregulation is expected to contribute to an increase in yield or biomass.

In an embodiment, this disclosure provides a method for increasing the yield or biomass of a plant or crop comprising inducing or over expressing the genes that are shown to be upregulated in FIG. 8, or down regulating or deleting the genes that are shown to be down regulated in FIG. 8 or both.

In an embodiment, this disclosure provides a method for identifying gene biomarkers that can increase plant biomass in soil that contains low levels of nitrogen and wherein the soil is arid, comprising determining gene expression that is exclusively defined by a relationships of N and W, such as N/W or N×W.

In an embodiment, this disclosure provides a method of predicting plant biomass or yield comprising determining the expression of genes in the field or in the lab, wherein the genes are one or more of LOC_Os10g09240, LOC_Os12g29400 (ABA-response protein), LOC_Os05g31020 (eRF peptide change release factor), LOC_Os03g57240 (C2H2 Transcription factor), and LOC_Os01g51360 (Lipase), wherein up or downregulation of the genes as shown in FIG. 8, is indicative of whether plant biomass or yield will increase or decrease. The plant may be any plant. For example, in an embodiment, the plant may be a genus of *Arabidopsis*, *Oryza*, *Zea* or *Triticum*. As an example, a decrease in expression of LOC_Os10g09240 is predictive of an increase in biomass and yield (FIG. 4 and FIG. 8 table). As another example, an increase in expression of LOC_Os03g57240 (C2H2 Transcription Factor) is predictive of an increase in biomass and yield (FIG. 4 and FIG. 8 table). The converse would be applicable for decreasing yield or biomass. Predictions based on increase or decrease in the expression of other genes can similarly be made.

In an embodiment, this disclosure provides a method for affecting plant biomass comprising altering the expression of one or more of LOC_Os10g09240, LOC_Os12g29400 (ABA-response protein), LOC_Os05g31020 (eRF peptide change release factor), LOC_Os03g57240 (C2H2 Transcription factor), LOC_Os01g51360 (Lipase) wherein affecting the biomass can be increasing or decreasing and altering the expression can be over or under expression. The plant may be any plant. For example, in an embodiment, the plant may be a genus of *Arabidopsis*, *Oryza*, *Zea* or *Triticum*. As an example, down regulating or deleting gene LOC_Os10g09240 would promote higher yield and biomass. As another example, over expressing or up regulating gene LOC_Os03g57240 would promote higher yield and biomass. The converse would be applicable for decreasing yield or biomass. Altering the expression of other genes to increase biomass or yield can similarly be made.

The disclosure is further illustrated by the following examples, which are not intended to be construed as restrictive.

Example 1

Figure 5:
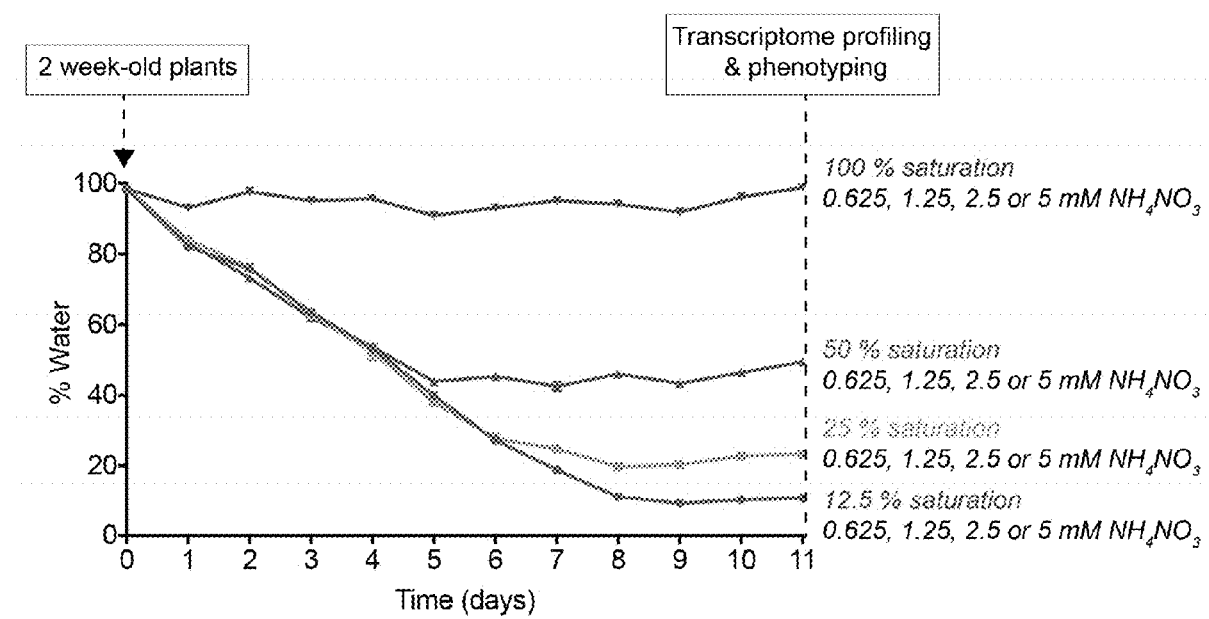
FIG. 5. Execution of the 4-by-4 factorial N-by-W matrix design varying N-mole and W-volume treatments. The 4-by-4 factorial N-by-W treatment matrix for rice seedlings varied both N and W amounts. To create these conditions, all treatment pots began at 100% W saturation with different N-concentrations. Evaporation was allowed to occur over time until each pot reached the desired W level—where W level was calculated through weighing each pot daily. W was then maintained at the desired saturation level through daily additions of W. Each pot condition was replicated in triplicate, resulting in 12 pots per W condition FIG. 6. Measuring the effects of combinations of N-moles and W-volume on rice seedling phenotype. A range of phenotypes were measured from rice seedlings grown under the experimental N-by-W design matrix treatment. We tested the ability for one of four models, each holding a single term, to explain phenotype. When a model significantly explained phenotype (p-value <0.05), the resulting adjusted $R^2$ is provided. We performed this analysis for A: shoot dry weight B: root dry weight C: water use efficiency D: leaf relative water content E: Percent of total $^{14}N$ assimilated in leaf tissue F: Percent of $^{15}NH_4$ assimilated in leaf tissue G: Percent of $^{15}NO_3$ assimilated in leaf tissue.

To investigate how plants sense and integrate N and W nutrient signals at the gene regulatory level, we grew rice seedlings in a 4-by-4 factorial matrix of continuous N and W dose combinations, and monitored plant phenotype and gene expression responses (FIG. 1A, FIG. 5, see Methods). Our 4-by-4 matrix varied both N-moles (supplied as $NH_4NO_3$) and W-volume. The highest amounts of N and W were chosen to promote plant growth, and the lowest amounts were chosen to limit plant growth. By varying N and W simultaneously, this matrix design allowed us to determine how rice plants sense and respond to N-moles, W-volume and N-molarity (N-moles/W-volume).

Figure 6:
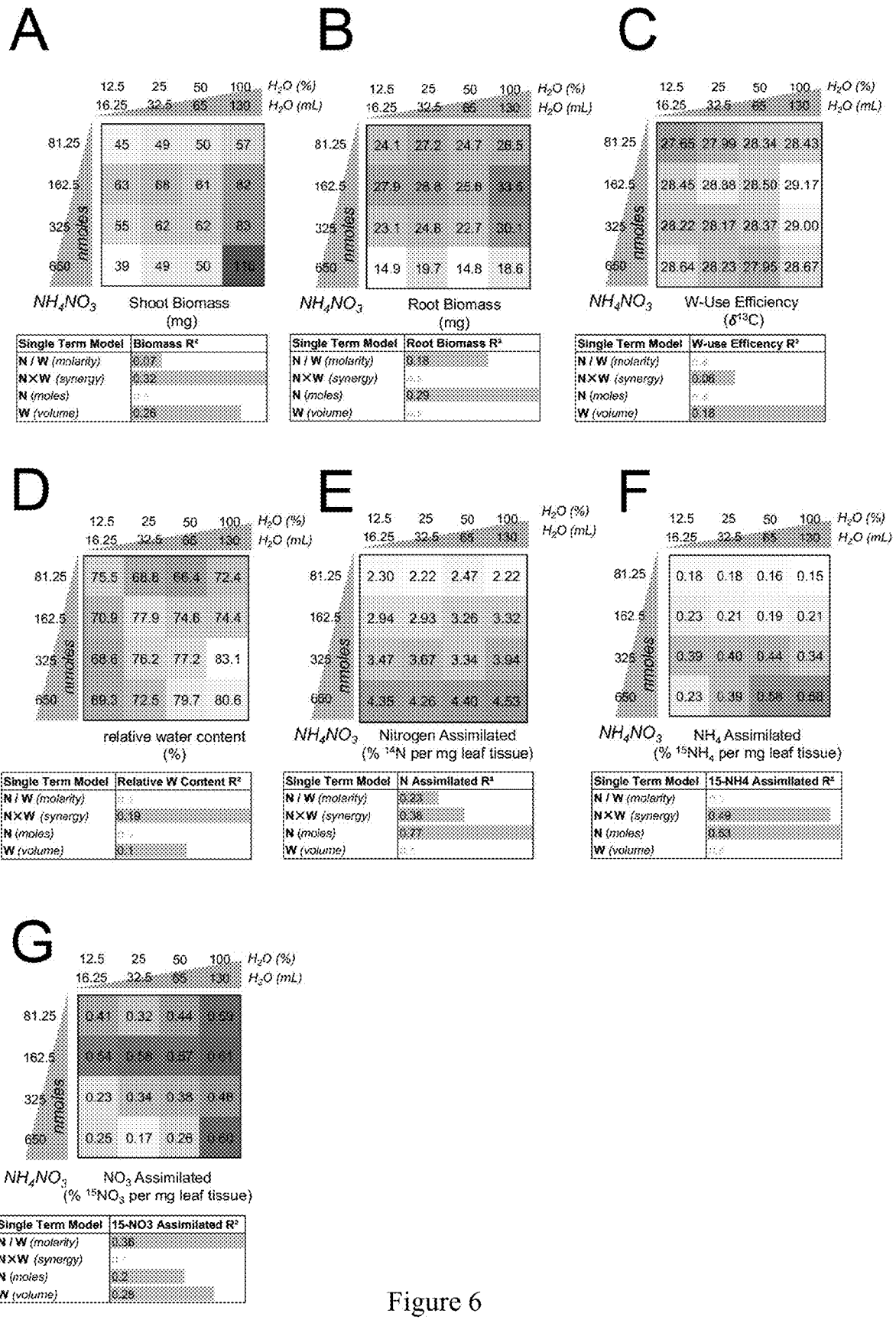

Rice seedlings were initially grown for 14 days on N- and W-replete media. Then, after 11 days of exposure to our matrix that varied N and W doses, we measured plant phenotypes (FIG. 1B, FIG. 6), and assayed leaf transcriptomes by RNA-seq. Our measurements of plant $\delta^{13}C$, a proxy for water use, were proportional to the amount of external W provided. Similarly, we found total leaf N-content (a combination of assimilated ammonium and nitrate) was proportional to the amount of external N-moles provided (FIG. 6). Together, these data indicated that internal leaf N- and W-status reflected their respective amounts in the external environment.

By observing phenotype, it was evident that seedlings within our growth matrix integrated N and W signals. Specifically, we found that changes in shoot biomass could be modeled by a synergistic interaction between N-moles and W-volume–N-moles×W-volume (FIG. 1B). We dubbed this N×W effect on biomass 'molar synergy' (FIG. 1B).

This effect—where phenotype could not be explained either by N or W alone—was also observed for the amount of N assimilated in leaf tissue, relative water content, and root biomass (FIG. 6)

Changing levels of gene expression allows plants to adapt to the abiotic environment. To understand how N and W signals are integrated at the gene regulatory level, we assayed the rice leaf transcriptomes of plants treated within our factorial matrix by RNA-seq. Using the following linear equation, we then modeled how each gene responded to N and W inputs genome-wide:

$$gene_a \text{ expression} = N + W + N \times W + \frac{N}{W} + c$$

This model assessed if a gene's expression can be explained by a linear dose response to N or W amounts, or a non-linear combination of the two (N×W). Though not typically included in linear models, the divisive term—N/W—was required to capture genes that could be responsive to N molarity. When M, representing N molarity (N/W) is substituted for N, which represents N moles in the above equation (if M=N/W), then $$gene_a \text{ expression}=M+W+MW+MW^2+c$$

We fit all expressed genes within the rice genome with this full linear model in DESeq2, and through subsequent steps of model simplification, each gene could be binned into one of 14 simplified forms of the equation (FIG. 1C). We found that the expression of 64% of regulated genes (6,739 genes) could be explained by a single term—either N-moles, W-volume, N-molarity (N/W), or molar synergy (N×W) (FIG. 1D). Analysis of genes explained by these four models provided insight into how plants integrate N and W signals at the gene regulatory level.

Moles of N or W: We found genes that responded exclusively either to the molar amounts of N or volume of W available.

Figure 2:
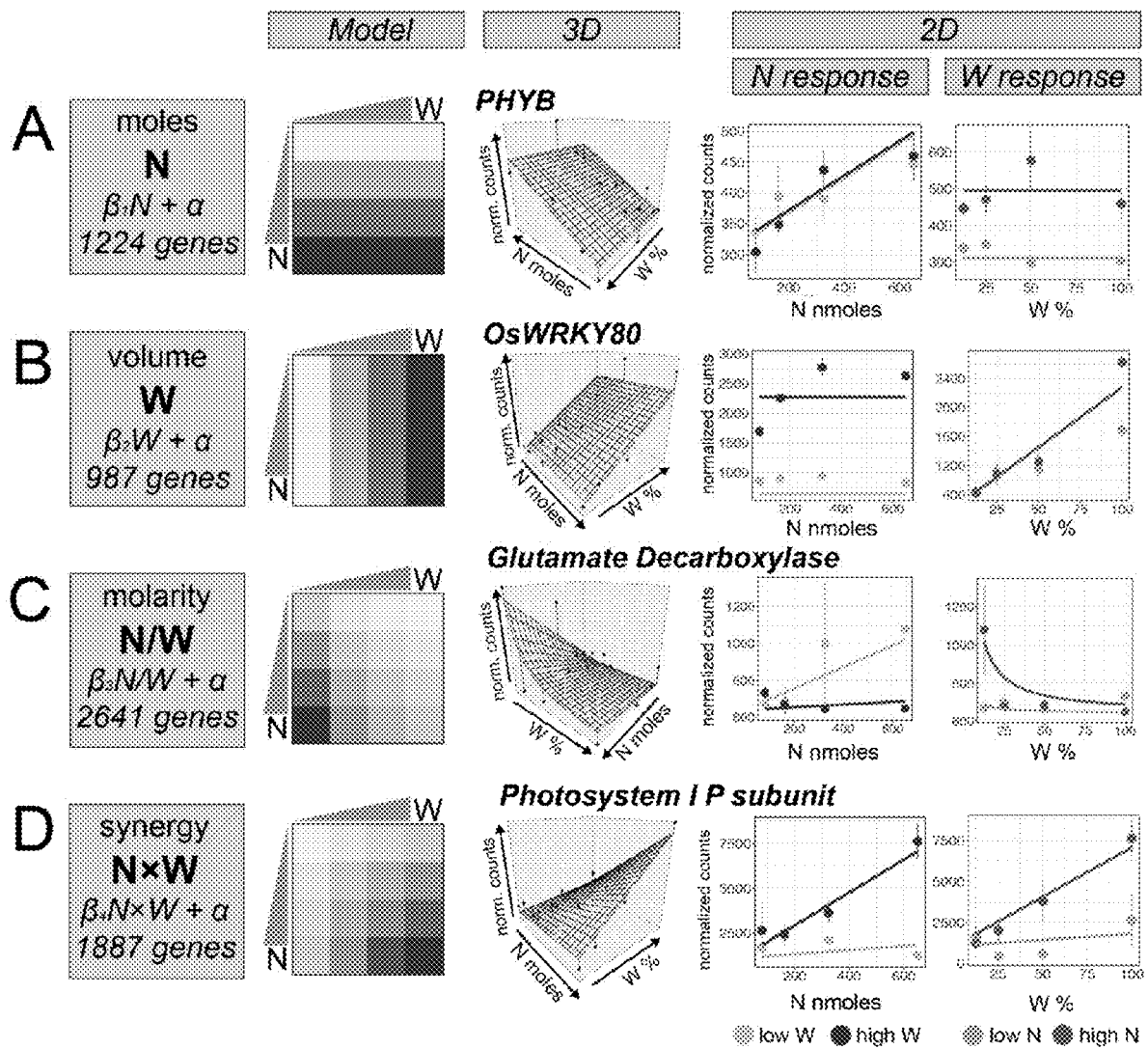
FIG. 2. Linear modeling of genome-wide expression data uncovers four main responses to changes in N-moles and/or W-volume. A: Expression of 1,224 genes are dose-dependent on N-moles. PHYB expression, an example fitted by the N-moles model, is shown in 3D. PHYB is also plotted in 2D, showing its response to changes in N-moles under the lowest and highest W-volume provided, and showing its response to changes in W-volume under the lowest and highest N-mole amounts provided. B: Expression of 987 genes exhibit dose-dependent responses to changes in W-volume; OsWRKY80 is an example. C: Expression of 2,641 genes exhibit dose-dependent responses to changes in N-molarity (N/W); glutamate decarboxylase is an example. D: Expression of 1,887 genes respond synergistically (N×W) to changes in N and W doses; photosystem 1 P-subunit is an example.
Figure 3:
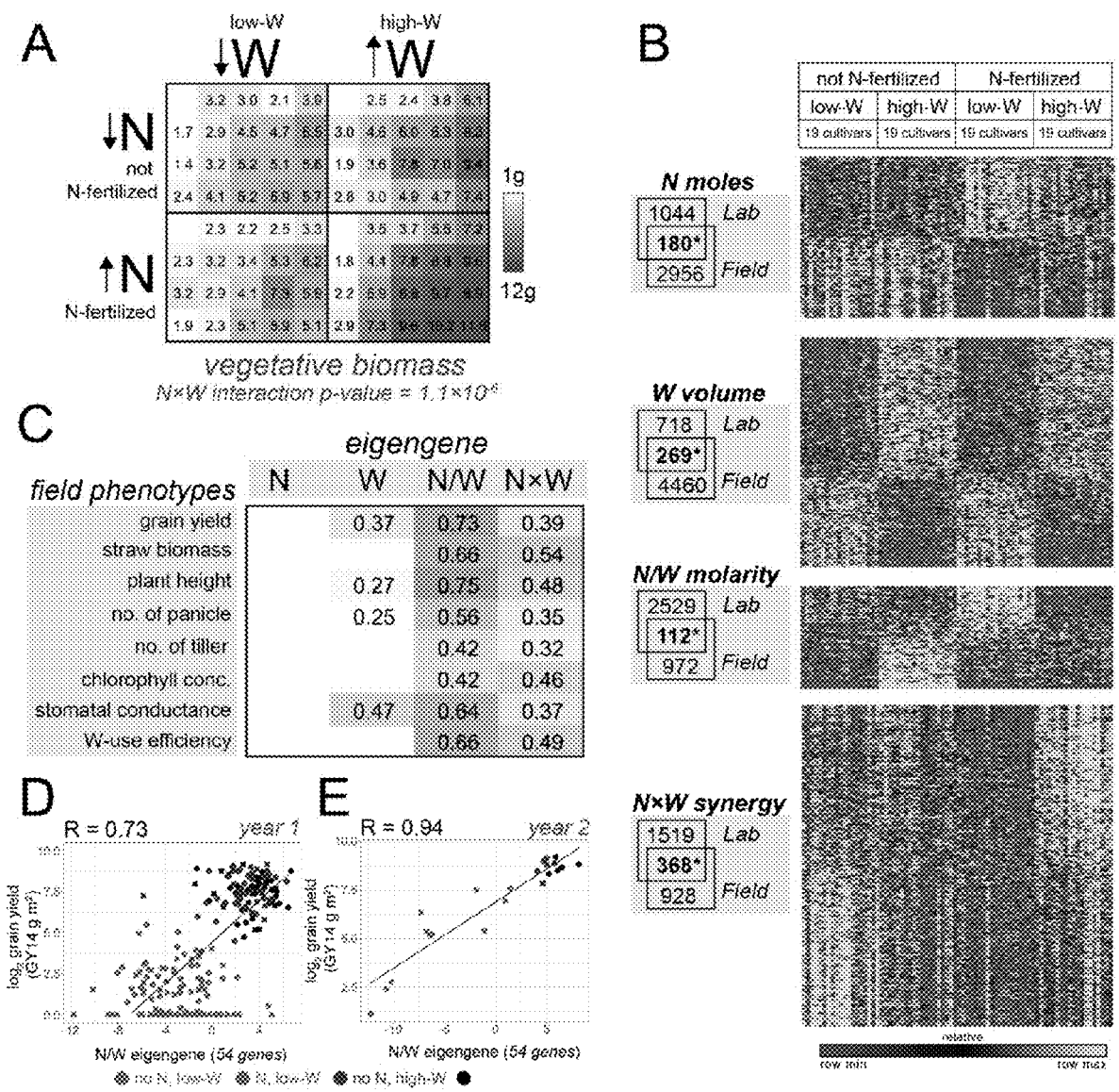
FIG. 3. Genes responding non-linearly to combinations of N-fertilizer and W-treatment are associated with agricultural outcomes. A: 19 rice cultivars were grown in the field under a matrix of four N- and/or W-treatments; each cell indicates the average biomass of each of the 19 rice cultivars. The synergistic interaction N×W could best explain differences in shoot biomass (3-way ANOVA interaction term p-value=$1.1\times10^{-6}$) B: The gene classes responding to combinations of N- and/or W-dose in rice seedlings found under laboratory conditions overlap significantly with reciprocal classes found in field grown plants (*Monte Carlo test p-val <0.05). Normalized expression patterns of lab-field validated genes are displayed in heatmap. C: Eigengenes derived from each gene set were correlated with crop traits. Significant R values are shown in red (permutation test, p-value <0.05). D: Example from C. Changes in N/W eigengene expression across 228 field samples is associated with grain yield. E: N/W eigengene expression is predictive within an independent field test set.

1,224 rice genes responded exclusively to N-moles in a dose-dependent manner, independently of W-volume (FIG. 1D, FIG. 2A). This class of N-mole response genes contained known N-responsive genes involved in N-uptake and assimilation such as the ammonium transporter OsAMT1 and glutamate synthase (GOGAT). It also contained novel N-responsive genes, including phytochrome PHYB, a light sensor and signal transducer (FIG. 2A). This N-mole response gene class was over-represented in N-relevant gene ontology (GO) terms such as 'N-compound metabolic process', and 'amine biosynthetic process'. Additionally, the majority of N-dose response genes (94%) significantly correlated with leaf N-content (FIG. 1D).

987 rice genes responded to W-volume in a dose-dependent manner, independently of N-moles (FIG. 1D, FIG. 2B). This class of W-volume response genes included genes implicated in drought responses, including rice orthologs of *Arabidopsis* genes involved in abscisic acid signaling (ABF2) and biosynthesis (AAOs 1-4), as well as OsWRKY80, a member of the WRKY transcription factor family involved in water responses (FIG. 2B). Furthermore, genes within this W-volume class significantly correlated with leaf W-use efficiency measurements ($\delta^{13}C$), while other classes showed little to no association (FIG. 1D).

Our genome-wide models also uncovered genes that respond to interactions between N-moles and W-volume, N-molarity (N/W) or molar synergy (N×W), as described herein.

Molarity (moles N/volume W): Our analysis uncovered 2,641 genes that specifically responded to N-molarity (N/W) (FIG. 1D, FIG. 2C). This set of genes was significantly enriched in N-related GO-terms including 'N-compound metabolic processes'. Members of the N-molarity response class included the N-assimilation genes aspartate aminotransferase and glutamate decarboxylase (FIG. 2C).

Thus, by uncoupling genome-wide responses to N and its solvent W, we discovered that plants can respond to dose changes in N-moles (FIG. 2A), W-volume (FIG. 2B) or N-molarity (FIG. 2C). These findings present a new insight of nutrient dose responses, as prior studies have not addressed whether nutrient dose is responded to either as absolute moles or molarity.

A biological reason why plants might regulate genes in response to N moles is because they require a direct indication of the absolute amount of nutrient available for plant growth and development. N molarity cannot provide this information—it is only a relative indication of N with respect to W. This effect was evident within our factorial treatment matrix. Significant changes in shoot biomass occurred only when absolute molar amounts of both N and W were non-limiting—seedling growth did not correlate significantly with N-molarity. Molar Synergy (moles N×volume W): Changes in biomass could be best modeled by the synergistic interaction between N and W: N×W (FIG. 1B).

Just as shoot biomass increased non-linearly with additions of N and W, we discovered 1,887 genes whose expression is explained by the synergistic interaction N-moles×W-volume (FIG. 2D). 55% of genes within this 'molar synergy' class significantly correlated with changes in biomass of rice seedlings—the highest proportion of any class (FIG. 1D). Upregulated genes within this N×W molar synergy gene class were enriched in GO-terms related to growth, such as 'photosynthesis' and 'translation', and members included 7 ribosomal subunits and the rice ortholog of the *Arabidopsis* Photosystem I P-subunit (FIG. 2D). Conversely, downregulated genes in this 'molar synergy' class were associated with stress, and were enriched in GO-terms such as 'apoptosis' and 'programmed cell death'.

Thus, synergistic gene regulatory responses to N-moles and W-volume may be a mechanism by which plants signal growth responses when absolute amounts of both N and W are optimal. Gene expression that is dependent on a multiplicative, non-linear interaction between N and W can ensure linear changes in both N or W amounts have non-additive outcomes on expression levels and phenotypes.

Taken together, these results indicate that the absolute amounts of N and W within the environment can be signaled at the gene expression level, as well as integrated in one of two ways. They can either be integrated 'biochemically', where W acts as a solvent, causing N to be sensed as N-molarity (N/W). In this instance, adding more W has a negative 'diluting' effect on N-molarity sensing. Alternatively, N and W can be integrated 'synergistically' (N×W), where N and W act as concurrent amplifying signals, causing the addition of more W to increase the response to N, and visa-versa.

Next, we investigated how sensing and integrating N and W signals informs agricultural performance of rice in the field. To answer this, we grew 19 different rice cultivars in the field at the International Rice Research Institute in the Philippines. Each rice cultivar was grown in a 2-by-2 factorial matrix that varied N-fertilizer and W-volume. Crops were N-fertilized at a high dose of 150 kg/ha, or not fertilized. Under each N condition, crops were grown either under W-replete vs. -deplete conditions, creating well irrigated or drought conditions (FIG. 4A). For the 228 samples generated, we assessed vegetative and yield phenotypes, and took vegetative leaf samples for RNA-seq analysis.

To investigate whether the same N-by-W gene expression patterns we identified under laboratory conditions (FIGS. 1 & 2) were present under field conditions, we assessed whether genome-wide expression patterns in rice field samples could be explained by N-fertilizer amount, W-treatment, or the interaction between the two (where genotype was treated as a covariate within the model). By these means, we found that the genome-wide expression patterns across 19 rice cultivars tested in the field were consistent with the four modes of nutrient responses we discovered in seedlings under laboratory conditions—N, W, N/W, N×W (FIG. 4B). Moreover, we found that the overlaps of lab-field gene sets for each gene class were significantly higher than expected by chance (FIG. 4B). These data support that rice's ability to discriminate between N-mole (N) and N-molarity (N/W) availability exists under both lab and field conditions.

To investigate whether the same N-by-W gene expression patterns we identified under laboratory conditions (FIGS. 1 & 2) were present under field conditions, we assessed whether genome-wide expression patterns in rice field samples could be explained by N-fertilizer amount, W-treatment, or the interaction between the two (where genotype was treated as a covariate within the model). By these means, we found that the genome-wide expression patterns across 19 rice cultivars tested in the field were consistent with the four modes of nutrient responses we discovered in seedlings under laboratory conditions—N, W, N/W, N×W (FIG. 4B). Moreover, we found that the overlaps of lab-field gene sets for each gene class were significantly higher than expected by chance (FIG. 4B). These data support that rice's ability to discriminate between N-mole (N) and N-molarity (N/W) availability exists under both lab and field conditions.

Next, we investigated whether expression levels of gene classes that were directionally-conserved (i.e. induced or repressed) across both laboratory and field settings were associated with cultivar agronomic performance. To do this, for each gene set—N, W, N/W, N×W—we calculated the first principle component, which represented the expression trends of all gene members in a single profile or 'eigengene'. Each resulting eigengene thus represented the set of lab-field validated genes responding either to N-moles (59 genes), W-volume (178 genes), N-molarity (N/W) (54 genes), or molar synergy (N×W) (184 genes)—where each eigengene accounted for 34%, 24%, 36%, and 27% of the proportion of variance in gene expression, respectively. We then assessed whether the expression profile for each of the four eigengenes were associated with field phenotypes across the 19 rice cultivars. The significance of this association was calculated by comparison to a null distribution of 10,000 eigengenes, generated from randomly selected genes expressed in the field.

This eigengene analysis revealed that the expression of genes regulated non-linearly in response to combinations of N and W doses—N/W and N×W—were significantly associated with traits important to crop production (FIG. 4C,). Genes responding synergistically to N and W doses (N×W) and to N-molarity (N/W) across the lab-field divide were significantly correlated with complex traits such as grain yield, straw biomass, plant height, number of panicles and number of tillers. Moreover, they were associated with N and W-related traits such as chlorophyll concentration, stomatal conductance and W-use efficiency (FIG. 4C).

Individual gene expression patterns of genes within this class were also more predictive of these phenotypes compared to other classes (FIG. 4).

Discovery of biomarkers that predict rice growth and yield can be targeted to make both W use efficient and N use efficient rice crops simultaneously, and thus meet the demand to adapt crops to low N, dry marginal soils. Our gene expression biomarkers are remarkably robust, reporting shoot dry weight outcomes both in seedlings grown in lab conditions and mature crops in the field across a range of indica and *japonica* rice varieties.

Figure 11:
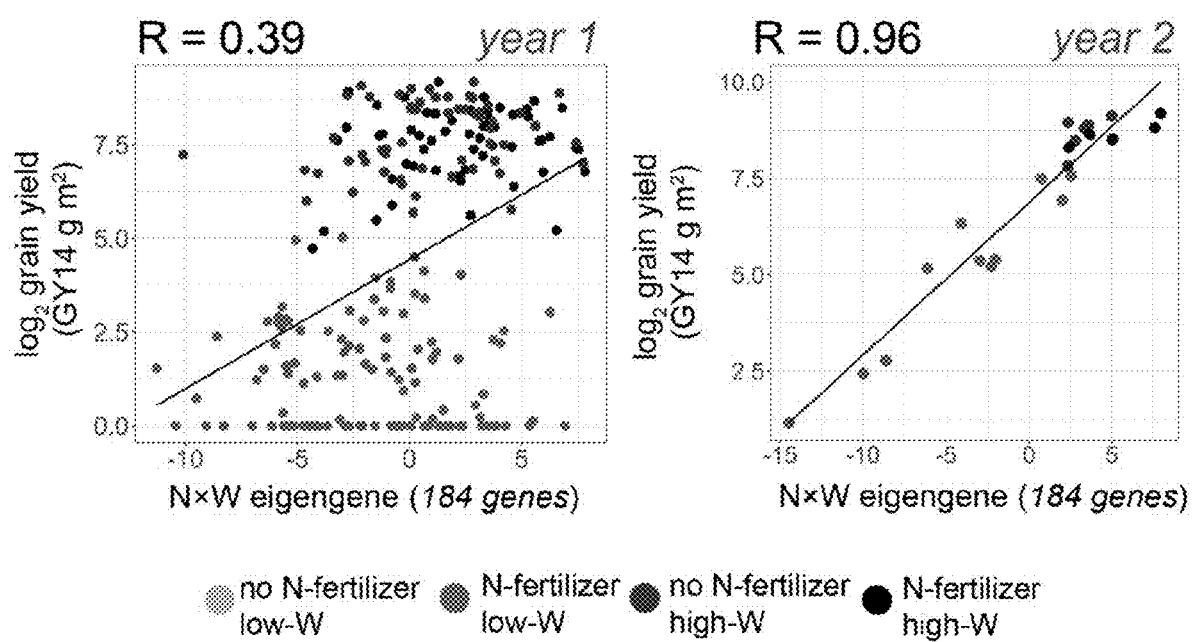
FIG. 11. N×W eigengene expression is predictive of crop outcome measures within an independent, replicated field test. A: Changes in N×W eigengene expression across 228 field samples is significantly associated with grain yield (permutation test, p-value <0.05). B: N×W eigengene expression is predictive of grain yield within an independent field test set observed the following year (permutation test, p-value <0.05).

Our insight that N/W and N×W gene sets, identified in both lab-grown seedlings and field-grown mature plants, were associated with final grain yield could be of particular use to rice breeders. To confirm that expression of these genes are associated with yield, we repeated our field experiment the following year (FIG. 11), and sequenced the transcriptomes of 2 genotypes that varied in their yield outcomes. Through repeating our eigengene analysis on this independent field data test set, we validated that N/W and N×W gene expression were each significantly associated with grain yield (FIGS. 4D & 4E, FIG. 11).

Materials and Methods

N and W Factorial Experiment: In this experiment, we grew rice seedlings within a 4×4 factorial treatment matrix varying Nitrogen (N) and Water (W) doses. This approach was designed to assess plant responses to changes in N-doses in a changing W-environment (varied by evaporation) (FIG. 1A). To create these treatment conditions, rice seedlings (Nipponbare) were first grown for 2 weeks on Yoshida media, supplemented with 5 mM $NH_4NO_3$, under 12 hour light (150 $\mu mol^{-2}$ $s^{-1}$)/12 hour dark diurnal cycle, at temperatures 27° C. and 25° C. respectively, 70% humidity. Endosperms were then removed, and 3 plants were transferred to each pot containing 680 g of sand, which could hold a maximum of 130 mL of W. To create distinct N-dose conditions, each pot contained 130 mL of one of four $NH_4NO_3$ concentrations (0.625 mM, 1.25 mM, 2.5 mM, 5 mM) in Yoshida media. 1% of N atoms were labelled either as $^{15}NH_4$, $^{15}NO_3$ or $^{15}NH_4^{15}NO_3$. Plants were maintained at complete pot saturation (130 mL) for 3 days. To create distinct W-doses, W was allowed to evaporate off pots, and the amount of W lost was calculated by weighing each pot daily (FIG. 6). Evaporation of W caused the molarity of N within the pot to increase, without changing the total N-moles present. Once the target W-saturation was reached, saturation was maintained by daily additions of W. In this way, four W-volumes were achieved—16.25 mL, 32.5 mL, 65 mL and 130 mL—which corresponded to four W-saturation levels—12.5%, 25%, 50%, 100% (FIG. 6). This approach created a 4×4 factorial matrix of 16 unique N and W dose treatment combinations. Each N by W dose treatment combination was tested in triplicate, resulting in 48 samples for RNA-seq analysis.

RNA-seq libraries were made using the NEB-next and sequenced using Next Seq Illumina platform. Genes with low read counts were removed and remaining libraries normalized by quantile normalization. Multivariate gene modeling on read counts for each of the remaining genes was performed in R, using DESeq2 starting with the full generalized linear model:

$$gene_a \text{ expression} = \alpha + \beta_1 N + \beta_2 W + \beta_3 N/W + \beta_4 N \times W$$

Where $\beta$ indicates each factors coefficient, $\alpha$ the intercept, and $gene_a$ expression for the normalized read counts.

After the full linear model was fit to the RNA-seq read counts of each gene (using design~N+W+N/W+N×W), we performed model simplification as follows: 1) Using the 'LRT' command, an FDR adjusted p-value was computed for each of the factors within the model across all fit genes. 2) If a gene were fit significantly by all four terms (adjusted p-value <0.005), then this gene was deemed fit by the full model and removed from remaining model simplification steps. 3) For all remaining genes, the factor with the least significance (highest FDR corrected p-value) was removed, and the model was refit with the remaining terms. This allows for one of four variations of a simplified model to be fit for each gene. 4) If a gene was fit significantly by all three terms (all three factor FDR corrected p-values <0.005), then this gene was deemed fit by a three-term model and removed from remaining model simplification steps. Steps 3 and 4 were repeated, fitting two term and one term models. If a gene was not fit by any model form, then it was removed from further analysis.

For genes with expression patterns best explained by a single model term, a gene expression heatmap of log-normalized reads was created using GENE-E software, displaying the relative expression levels for each gene (FIG. 1D). The normalized expression level of each gene within the heatmap was also correlated with shoot biomass, N-content and W-use efficiency (Pearson correlation), where significant associations (FDR adjusted p-value <0.05) were colored. The number of genes that correlated with shoot biomass in each class were 8, 421, 205, 1038 for classes N, W, N/W, N×W, respectively. The number of genes that correlated with N-content in each class were 1154, 0, 800, 1365 for classes N, W, N/W, N×W, respectively. The number of genes that correlated with W-use efficiency in each class were 0, 195, 0, 2 for classes N, W, N/W, N×W, respectively. GO Term analysis for each gene response class was performed in rice VirtualPlant Rice (virtualplant.org) using the full rice genome as the background set.

Field Study 19 rice cultivars (listed in FIG. 7) were grown under field conditions at the International Rice Research Institute CIRRI) at Los Banos, Philippines (July-December 2016). Each cultivar was supplied with either a N-replete dose of 150 kg/ha dose of $(NH_4)_2SO_4$ or with no N-treatment (N-deplete), 23 days after sowing (DAS). Under each N condition, fields were either W-replete, or W-deplete, the latter obtained by draining the field of W and protecting the field from rain (intermittent watering of W-deplete fields was required to sustain growth). For W deplete conditions, the minimum soil water potential was −34 kPa (non N-fertilized) and −52 kPa (N-fertilized) at 74 DAS (as measured by tensiometers at 30 cm depth). For each N and W condition, rice cultivars were grown in triplicate in a randomized block design, where each triplicate contained 20 plants. For each of the 19 rice cultivars, leaf transcriptomes at 49 DAS were sampled at the vegetative stage from 2 individual rice plants in biological triplicates per condition, 2 hours after dawn (n=228). Leaf tissue was stored in RNA later solution (Thermo Fisher Scientific) immediately upon sampling. Additionally, 2 rice plants were sampled for shoot dry weight 49 DAS per field treatment per genotype. A 3-way ANOVA function with three categorical variables— W, N and genotype—was performed on vegetative shoot dry weight. This model reported a significant positive interaction between N and W factors on biomass (p-value=$1.091 \times 10^{-6}$) (FIG. 4A).

From vegetative rice samples, additional traits were measured as follows: W-use efficiency was measured from leaf tissue using $\delta^{13}C$ isotopic discrimination by mass spectrometry (performed by IRRI Analytical Services Lab, 3 plants per replicate). Tiller number was counted by hand from each vegetative sample (n=2 per treatment per genotype). Chlorophyll concentration index was measured 55 DAS (CCM-200 Chlorophyll concentration meter, Apogee Instruments, 2 plants per replicate). Stomatal conductance was measured on two leaves per plot, averaged over two separate days, 45-48 DAS (AP4 porometer, Delta T Devices, 2 plants per replicate).

End point phenotyping for biomass, plant height, panicle number and grain yield were measured as follows: Straw biomass was measured as total straw dry weight (g) from a plot divided by the sampling area ($m^2$). Panicle number was recorded by hand from 6 plants per genotype per treatment. Days to flowering was counted as the length of time, in days from sowing, until half the plants in each replicate plot had visible panicle emergence. Ranges measured between 61-124 DAS. Plant height was measured in centimeters, from the base of the plant to the tip of longest leaf. Grain yield was measured as the aggregate grain amount per cultivar in each triplicate using the following formula:

$$\text{grain yield} = (\text{grain weight} \times ((100 - \text{moisture content})/86))/\text{sampling area}$$

Figure 10:
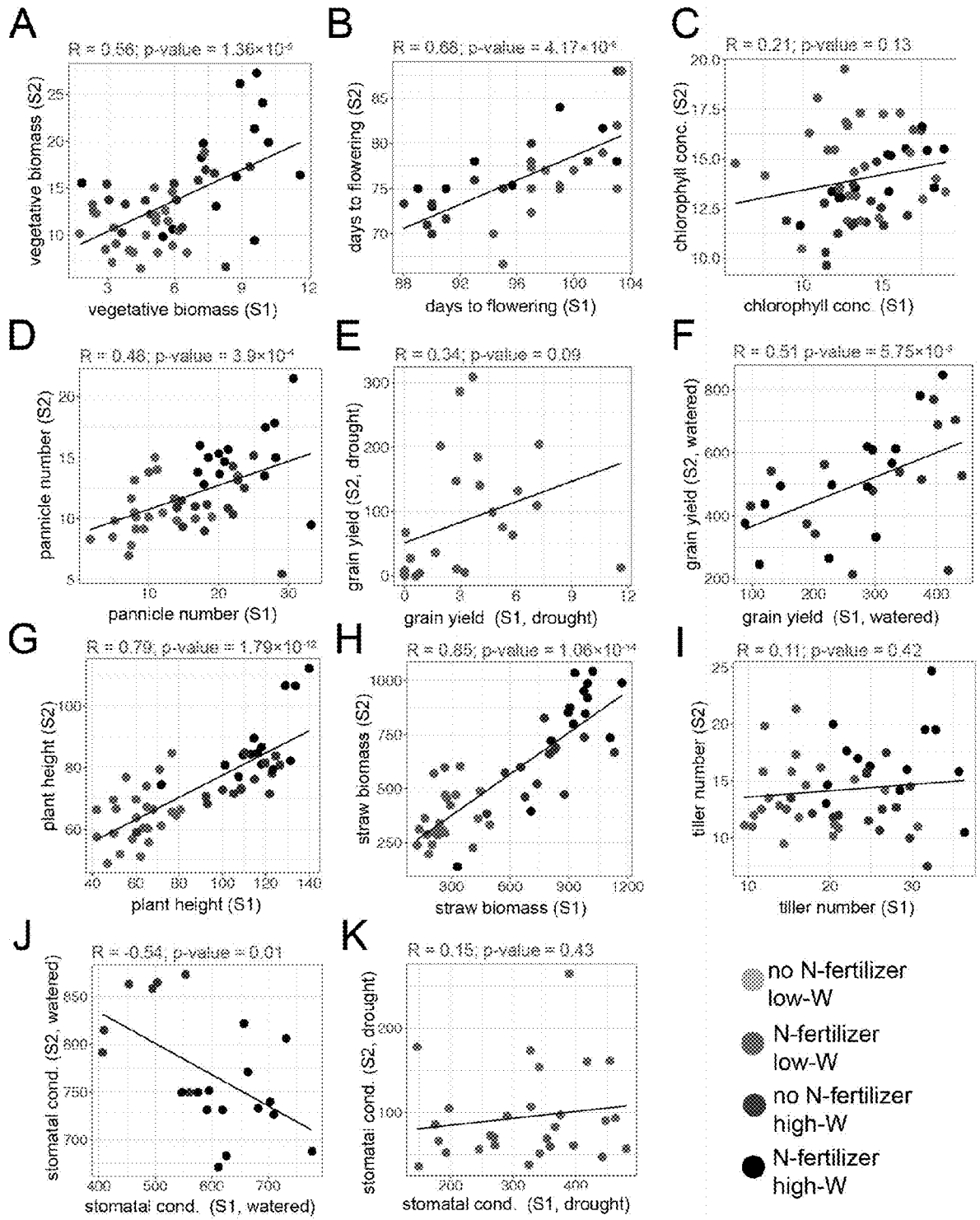
FIG. 10. Testing reproducibility of field phenotypes. For 14 of the 19 cultivars tested, we duplicated our field experiments at the International Rice Research Institute in the Philippines (July-December 2017). We found that phenotypes between the 2016 ('S1') and 2017 ('S2') seasons were largely reproducible, as demonstrated through Pearson correlation analysis. Grain yield (E and F) and stomatal conductance (J and K) observations were separated into well-watered or drought treated before correlation analysis.

To ensure our field trial phenotypes were reproducible, we replicated the experiment for 14 out of the original 19 cultivars at IRRI the following year (July-December, 2017). In this season, for W-deplete conditions, the minimum soil water potential was −27 kPa (low N) and −59 kPa (high N) at 73 DAS. We observed grain yield, vegetative biomass, final (straw) biomass, chlorophyll concentration, stomatal conductance, days to flowering, plant height, tiller number and panicle number using the same techniques as the previous year. We then correlated these second season outcomes with that of the first (FIG. 10).

Additionally, at 49 DAS we collected leaf tissue samples for RNA-seq analysis from two cultivars IR-64 and IR83388-B-B-108-3, for transcriptomic analysis. We selected these lines because of their differing responses to N and W in the previous year's sampling of 19 rice cultivars.

From libraries generated from the field experiments (described in section 1.3), we removed from our analysis genes with total read counts below 128 (summed across all conditions).

A 3-way ANODEV function with three categorical variables—W, N and Genotype—was called on read counts for each gene detected in field samples using DESeq2[15] (design~N+W+N:W+Genotype). A gene was considered differentially expressed when either N, W or N:W terms within the model scored below FDR-corrected p-value of 0.05. We note the Genotype factor was used to control for the effects between cultivars, but not used for sub-setting the data.

A gene was binned as N-responsive or W-responsive when either respective term was significant, while the other term as well as the interaction term between N and W (N:W) was not (FDR-corrected p-value >0.05). If the interaction term was significant, a gene was binned as N×W when the N and W interaction term $\log_2$ fold change was positive, and binned as N/W when the $\log_2$ fold change was negative.

Specifically, a positive $\log_2$ fold change indicated that differential gene expression occurred under high-W and high-N conditions, or low-W and low-N conditions. These genes were deemed N×W genes because this type of gene expression pattern agrees with N×W gene expression patterns found under laboratory conditions (where such genes were activated under high-N and high-W, or low-N and low-W treatments). The same logic applies to assigning N/W genes in the field. A negative $\log_2$ fold change value indicated that differential gene expression was driven by high-W and low-N conditions, or low-W and high-N conditions, a trend that N/W gene expression follows under lab conditions.

We used Monte Carlo simulations to assess the significance of the overlap between classes of dose response genes identified in the laboratory and field: N, W, N/W and N×W. As a background set for this analysis, we used the union of genes found either expressed under lab or field conditions. Monte Carlo simulations were performed in VirtualPlant using the GeneSect function (virtualplant.org). For heatmap visualization of lab-field validated gene sets (using GENE-E software), the expression value for each gene per cultivar in the field was first normalized to between 0 and 1, where 1 represented the maximum expression value (FIG. 4B).

We subsetted genes within each of the four classes—N, W, N/W and N×W—to include only those genes that were consistently regulated across laboratory and field conditions (i.e. induced or repressed in both experiments). We then calculated the first principal components, or 'eigengenes' of each of the lab-field validated gene classes using the field gene expression data, logged to the base 2. Principal components were calculated in R using the prcomp function, and each resulting eigengene was then correlated with $\log_2$ values of field phenotypes using Pearson correlation. Since direction of principal component eigenvectors are arbitrary with respect to sign, all correlation values are reported as positive correlations, regardless of the direction of the slope of correlation in plots. A p-value of the association between the eigengene and phenotype was calculated by comparison to a null distribution. This distribution was created by calculating an eigengene from a random gene set of the same sample size over 10,000 permutations. Only those eigengenes that passed a p-value cut-off of 0.05 were deemed significant.

Figure 9:
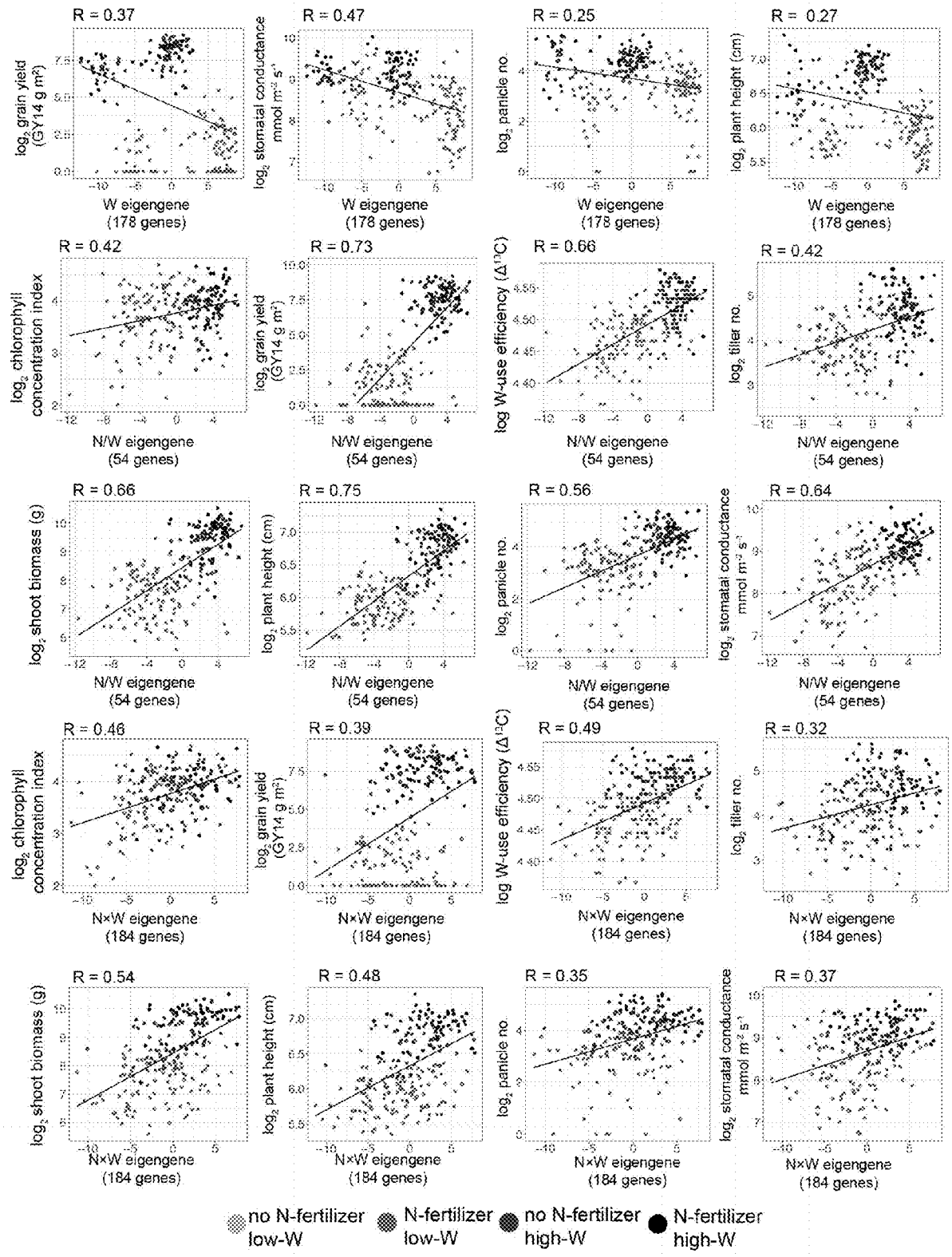
FIG. 9. Correlating lab-field validated eigengenes with field phenotypes. For each of our lab-field validated gene sets responding to N-moles (59 genes) W-volume (178 genes), N-molarity (N/W) (54 genes), or a synergistic response to N×W (184 genes), we reduced the expression trends of all gene members into a single profile or 'eigengene'. We then correlated each eigengene with field phenotypes. The significance of association was calculated by comparison to a null distribution of 10,000 random eigengenes. Significant associations (p-value <0.05) are shown here, with significant Pearson R-values displayed.

To test whether N/W and N×W gene expression was indeed predictive of yield outcomes indeed predictive of yield outcomes, we repeated our eigengene analysis using an independent test set. Specifically, we assessed whether eigengene expression of two cultivars (IR-64 and IR83388-B-B-108-3, see section 1.3) sampled the following year was associated with yield results. To achieve this, we normalized reads derived from these samples using DESeq2, and then computed the first principal component from the expression of the 54 and 184 genes that made up the N/W and N×W eigengene classes, respectively. We then correlated resulting eigengenes genes with yield outcome using Pearson correlation (FIG. 4E, FIG. 9). A p-value of the association between the eigengene and phenotype was calculated by comparison to a null distribution of 10,000 random eigengenes created from expressed genes in the field. This eigengene analysis indicated that resulting associations were significant (p-value <0.05).

The invention has been described through some embodiments. Routine modifications to the embodiments and the disclosure will be apparent to those skilled in the art and such modifications are intended to be within the scope of the disclosure.

What is claimed is:

1. An mRNA expression chip consisting of a substrate and polynucleotides that bind with specificity to mRNA transcribed from genes LOC_Os10g09240, LOC_Os12g29400, LOC_Os05g31020, LOC_Os03g57240, and LOC_Os01g51360, wherein the polynucleotides are attached to the substrate, and wherein the polynucleotides are each 26-5,000 nucleotides long, and wherein said polynucleotides are relevant for affecting plant biomass and whose expression is defined by N/W or N×W models.

2. The mRNA expression chip of claim 1, wherein the plant biomass comprises plants from a genus of *Arabidopsis, Oryza, Zea* or *Triticum*.

3. The mRNA chip of claim 1, wherein the polynucleotides are the cDNAs corresponding to the mRNAs.

* * * * *